(12) United States Patent
Hexsel

(10) Patent No.: US 9,220,717 B2
(45) Date of Patent: Dec. 29, 2015

(54) MEDICINAL COSMETIC LIPOATROPHY

(76) Inventor: Doris Hexsel, Porto Alegre (BR)

(*) Notice: Subject to any disclaimer, the term of this patent is extended or adjusted under 35 U.S.C. 154(b) by 653 days.

(21) Appl. No.: 13/810,022

(22) PCT Filed: Mar. 2, 2010

(86) PCT No.: PCT/BR2010/000059
§ 371 (c)(1),
(2), (4) Date: Jan. 14, 2013

(87) PCT Pub. No.: WO2010/099587
PCT Pub. Date: Sep. 10, 2010

(65) Prior Publication Data
US 2013/0116223 A1    May 9, 2013

Related U.S. Application Data

(60) Provisional application No. 61/209,065, filed on Mar. 2, 2009.

(51) Int. Cl.
| | | |
|---|---|---|
| *A61K 31/573* | (2006.01) | |
| *A61K 31/167* | (2006.01) | |
| *A61K 45/06* | (2006.01) | |
| *A61K 8/63* | (2006.01) | |
| *A61K 9/00* | (2006.01) | |
| *A61K 31/137* | (2006.01) | |
| *A61Q 19/06* | (2006.01) | |

(52) U.S. Cl.
CPC .................. *A61K 31/573* (2013.01); *A61K 8/63* (2013.01); *A61K 9/0019* (2013.01); *A61K 31/137* (2013.01); *A61K 31/167* (2013.01); *A61K 45/06* (2013.01); *A61Q 19/06* (2013.01); *A61K 2800/91* (2013.01)

(58) Field of Classification Search
None
See application file for complete search history.

(56) References Cited

U.S. PATENT DOCUMENTS

| 5,192,528 A * | 3/1993 | Radhakrishnan et al. ...... 424/45 |
| 2004/0141925 A1* | 7/2004 | Bosch et al. ...................... 424/46 |
| 2005/0143347 A1* | 6/2005 | Boderke et al. ................. 514/78 |
| 2005/0261258 A1* | 11/2005 | Kolodney et al. ............. 514/169 |
| 2006/0127468 A1 | 6/2006 | Kolodney et al. |
| 2006/0154906 A1 | 7/2006 | Kolodney et al. |
| 2006/0211665 A1* | 9/2006 | Ranawat et al. ............. 514/171 |

OTHER PUBLICATIONS

Tiso et al. disclose in The Spine Journal 4 (2004) 468-474.*
Schectman, A.D. in American Family Physician 77(10):1372 (2008).*
Basic and Clinical Dermatology' vol. 42, Anesthesia and Analgesia in Dermatologic Surgery, Edited by M. Harahap and A.R. Abadir (2008).*
Trojian et al. in American Family Physician 2007:76:86-89.*
'Kenalog-40' in packageinserts.bms.com/pi/pi_kenalog-40.pdf (retrieved from the internet Dec. 5, 2013).*
Ravaud et al. in Arthritis & Rheumatism 42(3), 475-482 (1999).*
Goodman and Gilman's The Pharmacological Basis of Therapeutics (Tenth Edition (2001), McGraw Hill, Chapter I, pp. 3-29.*
Amjad et al. in JCPSP 2005, 15(11), 683-685.*
Trojian et al. in American Family Physician 76(1), 2007, 86-89.*
Kang et al. in Dis Colon Rectum 2000:43:1288-1291.*
Nobutaka in Scand J Plast Reconstr Hand Surg 33:89-91, 1999.*
Hexsel et al.: "Cosmetic lipotrophy of the face", Journal of the American Academy of Dermatology, C.V. Mosby, St. Louis, MO, US; vol. 60, No. 3, Mar. 2009, p. AB185, XP025964614, ISSN: 0190-9622, DOI: 10.1016/J. JAAD.2008.11.805.
Donfrio et al.: "Techniques in Facial Fat Grafting", Aesthetic Surgery Journal, Mosby-Yearbook, St. Louis, MO, US, vol. 28, No. 6, Nov. 1, 2008, pp. 681-687, XP025794998, ISSN: 1090-820X, DOI: 10.1016/J. ASJ.2008.09.003.
Arnold et al.: "Forty-nine years of meetings of the American Academy of Dermatology:1938 to 1987", Journnal of the American Academy of Dermatology, C.V. Mosby, St. Louis, MO, US, vol. 18, No. 4, Apr. 1, 1988, pp. 862-874, XP023331451, ISSN: 0190-9622, DOI: 10.1016/S0190-9622(88)80080-X.
Database Embase [Online], Elsevier Science Publishers, Amsterdam, NL; Nov. 2003, Bak et al.: "A Case of Multiple Angiolipoma", XP002684253, Database accession No. EMB/2004053744.
Korean Journal of Dermatology 200311 KR, vol. 41, No. 11, Nov. 2003, pp. 1554-1556, ISSN: 0494-4739.

* cited by examiner

*Primary Examiner* — Dennis Heyer
(74) *Attorney, Agent, or Firm* — Lambert & Associates; Gary E. Lambert; David J. Connaughton, Jr.

(57) ABSTRACT

Methods relating to local injections of corticosteroids are provided. More specifically intralesional injections of corticosteroids and preferably Triamcinolone and its derivatives are suitable to produce medicaments to be injected in the subcutaneous fat at deep levels to provoke cosmetic lipoatrophy of small fat deposits on the face and body.

4 Claims, 5 Drawing Sheets

Figure 3                                    Figure 4
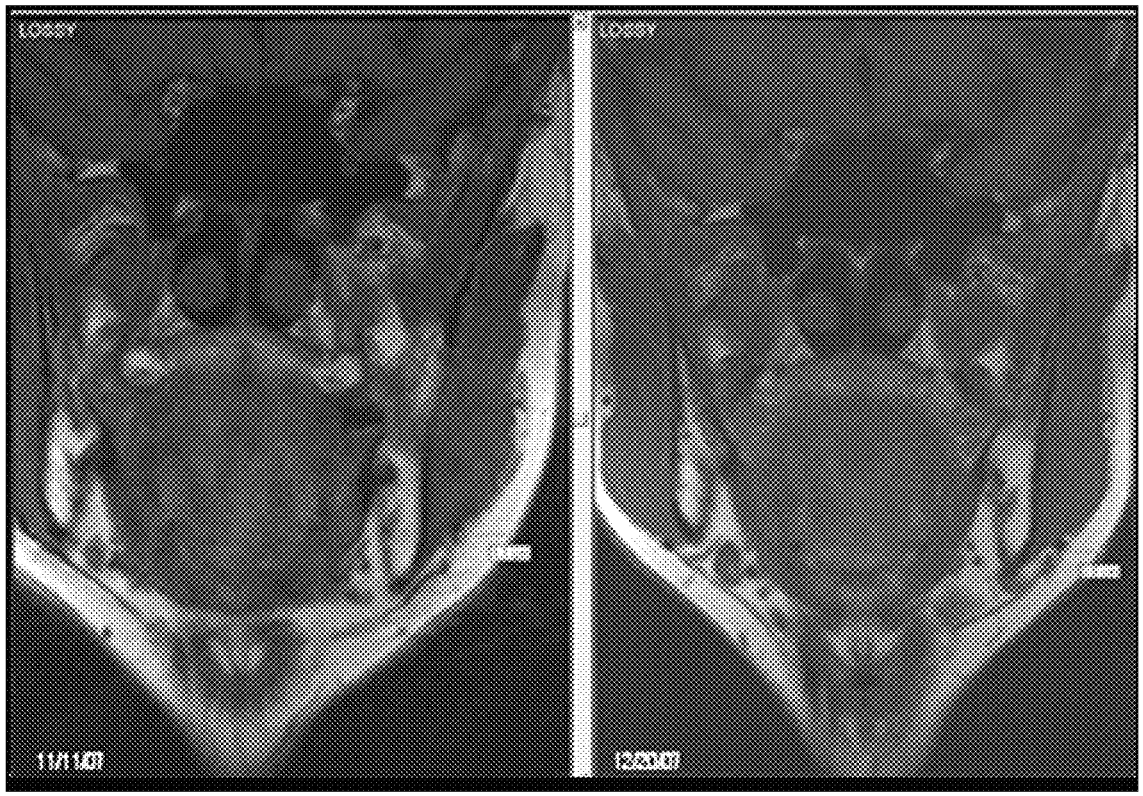

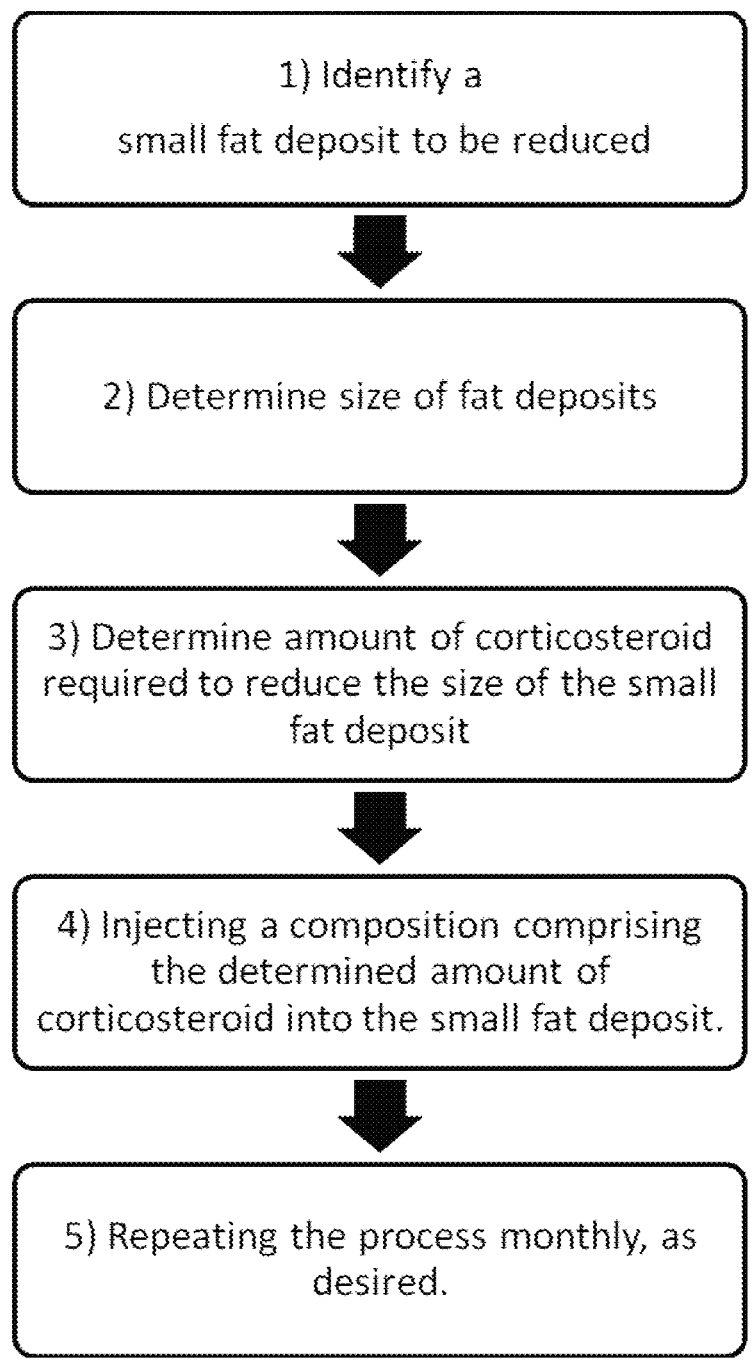

MEDICINAL COSMETIC LIPOATROPHY

CROSS REFERENCE TO RELATED APPLICATION

This application is for entry into the U.S. National Phase under §371 for International Application No. PCT/BR2010/000059 having an international filing date of Feb. 3, 2010, and from which priority is claimed under all applicable sections of Title 35 of the United States Code including, but not limited to, Sections 120, 363 and 365(c), and which in turn claims priority to Provisional Patent Application No. 61/209,065 filed on Feb. 3, 2009.

BACKGROUND OF THE INVENTION

1. Field of the Invention

The invention relates to a composition comprising at least one injectable corticosteroid and a diluent, preferable an anesthetic solution, which is suitable for producing medicaments to diminish small fat accumulations on the face and body by causing atrophy of the fat cells.

2. Description of Related Art

At present, subcutaneous accumulations of fat are treated by surgical means through liposuction or direct surgical removal. For small fat deposits, such those occurring with aging in some areas of the face, liposuction is too aggressive and is associated with the known complications or risks.

Injectable drugs, such as phosphatidylcholine (PPC) and sodium deoxycholate, also known as lipodissolve agents, were also used in some countries in the last few years (particularly in Brazil up to 2002), although there are no studies proving their safety and efficacy. Moreover, these drugs were also associated with severe side effects, including death in animals. (Paschoal, L H, Lourenco L, Ribeiro A, et al. *Um alerta! Efeitos sistêmicos e teciduais da fosfatidilcolina em suínos [poster]. Presented at 16° Congresso Brasileiro de Cirurgia Dermatológica. Porto de Galinhas* June, 2004)

US2005/0143347 describes a method for removing subcutaneous accumulation of fat as well as aqueous preparations comprising at least one phospholipid and/or at least one bile acid and a component assisting degradation of fat such as riboflavin. An anti-inflammatory compound can be added in the preparation.

The term "corticosteroids" means compounds from the adrenal cortex. In technical terms, corticosteroid refers to both glucocorticoids and mineralocorticoids (as both are mimics of hormones produced by the adrenal cortex), but is often used as a synonym for glucocorticoid. Glucocorticoids are a class of steroid hormones characterized by an ability to bind with the glucocorticoid receptor (GR) and trigger similar effects. Glucocorticoids are distinguished from mineralocorticoids and sex steroids by their specific receptors, target cells, and effects.

Glucocorticoids have potent anti-inflammatory and immunosuppressive properties. This is particularly evident when they are administered at pharmacologic doses, but also is important in normal immune responses. As a consequence, glucocorticoids are indicated for the treatment of many diverse conditions, including allergies, autoimmune diseases and inflammatory disease like asthma (*New England J Med* 2005; 353:1711-23).

Corticosteroids can be used topically, orally and by injections. Injectable corticosteroids currently used in medicine include the short-Acting injectable corticosteroids such as cortisone and hydrocortisone; the intermediate-Acting Injectable corticosteroids such as Prednisone, Prednisolone tebutate, Triamcinolone and Methylprednisolone its derivatives such as methylprednisolone acetate; the long-Acting corticosteroids such as Dexamethasone and its derivatives such as Dexamethasone sodium phosphate and Betamethasone its derivatives such as betamethasone dipropionate, betamethasone disodium phosphate and betamethasone acetate, and others.

Triamcinolone and other systemic corticosteroids have strong anti-inflammatory effects and this explains the large use of these compounds in medicine. At Medline, more than twenty-five thousands papers are published on injectable corticosteroids and more than five thousands papers on triamcinolone are published. Injectable corticosteroids are usually commercialized in stable aqueous suspension and are also described in the Patent Applications or patents such as U.S. Pat. No. 6,395,294 owned by Triesence (exploitation by Alcon) until Jan. 13, 2020 for Triamcinolone acetonide in intravitreal injectable form.

Triamcinolone acetonide injectable suspension USP (Kenalog®-40 Injection, Bristol-Myers Squibb Company, Italy) is a synthetic corticosteroid designed to provide systemic immunosuppressant and anti-inflammatory effects, as well as other intralesional or sublesional local effects for various skin diseases and conditions. The drug is stable at room temperature and must be shaken well before using.

Triamcinolone and/or other injectable corticosteroids are commonly used in dermatology for intralesional injections, as well as in other specialties and diseases, such as for joint inflammation and pain. Intralesional corticosteroids injections release a high concentration of the drug directly on the action site, with minimal systemic absorption. These drugs are considered very safe, low cost and efficient for an expressive number of diseases and conditions, for patients of different ages. Few applications and low doses are considered extremely safe, also for patients presenting severe diseases.

The aging process is caused by intrinsic and extrinsic aging, as well as changes in hard and soft tissues. Muscular hyperactivity causes dynamic wrinkles and is currently being treated by botulinum toxins; the losses in hard and soft tissues are currently being treated by fillers; the surface alterations are being treated by ablative and non-ablative techniques, as well as by topical retinoids and other active ingredients. There are no currently medical approved drugs for age-related fat accumulation. It is reported that fat pads like those occurring under the eyes, on the abdomen or on the hips of overweight people shrink, and there are said to be esthetic improvements in the appearance of the treated people, if these people received subcutaneous injection of Lipostabil® N I.V. (Patricia Guedes Rittes, *The Use of Phosphatidylcholine for Correction of Lower Lid Bulging Due to Prominent Fat Pads, Dermatol. Surg.* 2001; 27: 391-392). Residual small fat deposits are also common complaints after liposuction.

SUMMARY OF THE INVENTION

In the attempt to find effective compounds for nonsurgical removal of subcutaneous accumulations of fat, it has now surprisingly been found that subcutaneous administration of Triamcinolone and/or other corticosteroids, at low doses and few applications, which have to date been used for many diseases and conditions, also lead to a safe and effective regression of small fat deposits in the face and body.

The invention therefore relates to the use of a composition comprising:
  a) at least one corticosteroid
  b) optionally a diluent c) optionally at least one anesthetic solution with or without vasoconstriction agent
d) optionally one component to prevent skin atrophy
e) saline or physiological pH solution for producing a medicament to reduce small areas of subcutaneous accumulations of fat.

In an alternative and preferred embodiment, the invention relates to the use of a composition comprising:
a) at least one corticosteroid
b) optionally at least one anesthetic solution with or without vasoconstriction agent
c) optionally one component to prevent skin atrophy
d) saline or physiological pH solution for producing a medicament to reduce small areas of subcutaneous accumulations of fat.

The invention further relates to the use of a composition comprising:
a) at least one corticosteroid
b) optionally a diluent
c) optionally one component to prevent skin atrophy
d) saline or physiological pH solution for producing a medicament to reduce small areas of subcutaneous accumulations of fat.

In the context of the present invention, the composition may comprise more than one corticosteroid and for example two or more in combination in the same physiological medium.

The invention further relates to the use of a composition comprising:
a) at least two or more corticosteroids
b) optionally at least one anesthetic solution and
c) saline or physiological pH solution for producing a medicament for reduce small areas of subcutaneous accumulations of fat.

The invention further relates to the use of a composition comprising:
a) at least one or more corticosteroids
b) optionally a diluent
c) at least one anesthetic solution with or without vasoconstriction agent
d) at least one active ingredient to destroy fat, such as a phospholipids or deoxicholate
e) at least one component to prevent skin atrophy or the spread of the product
f) saline or physiological pH solution for producing a medicament to reduce small areas of subcutaneous accumulations of fat.

The invention further relates to the use of a composition comprising:
a) at least one corticosteroid
b) optionally a diluent
b) at least one anesthetic solution with or without vasoconstriction agent
c) component assisting degradation of the fat
d) at least one component to prevent skin atrophy
e) saline or physiological pH solution for producing a medicament to reduce small areas of subcutaneous accumulations of fat.

BRIEF DESCRIPTION OF THE DRAWINGS

FIG. 3 provides a view of an MRI exam performed before a single session of treatment with triamcinolone injections.

FIG. 4 provides a view of an MRI exam performed after a single session of treatment with triamcinolone injections.

FIG. 7 provides a flow chart of an embodiment of the steps involved in the method of treatment.

DETAILED DESCRIPTION

Figure 1:
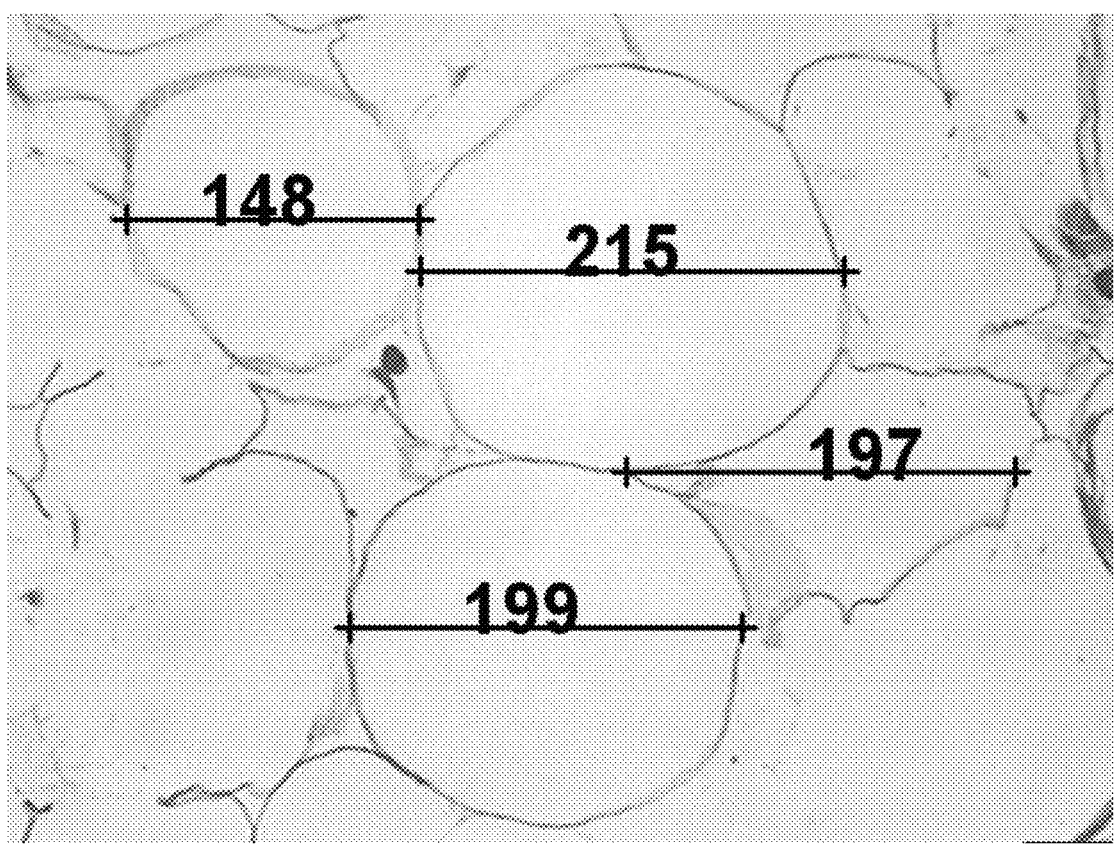
FIG. 1 provides a histologic picture which shows fat tissue with hematoxilyn-eosin stain before treatment and the measurements of some adipocyes in pixels using same magnification.

The invention further relates to the use of the compositions for producing a medicament for the treatment of small fat accumulations on the face and body, including residual areas of liposuction and other localized fat accumulation.

The invention further relates to the use of the compositions for producing a medicament for the treatment of derangements of fat distribution of an unwanted nature, such as raised areas of cellulite and fat related tumors.

One embodiment of the present invention is a method of decreasing or reducing small fat deposits by administering to an individual in need thereof, a sufficient amount of a composition comprising at least one injectable corticosteroid with a physiological acceptable medium. The said may further comprise at least one anesthetic agent and/or at least one component to prevent skin atrophy. In a preferred embodiment the said composition is administered to an individual in need by local injections in the subcutaneous fatty areas.

By diluent it is meant any acceptable diluent of the injectable corticosteroid which is preferably 0.9% saline or saline plus anesthetic solution, or anesthetic solution alone. Injectable anesthetic solutions as diluent are preferable to make the procedure less painful. The most frequent anesthetic solutions have lidocaine as the active ingredient, but bupivacaine and others may be used.

In another embodiment of invention, vasoconstriction agents are incorporated to injectable anesthetic solutions and thus help the active ingredient to remain at the injection site and increase the safe dose of the anesthetics. The most frequently used vasoconstriction agents are epinephrine and phenylephrine.

By physiological acceptable medium it is meant a medium compatible with intralesional or subcutaneous injection. This medium can be prepared in advance or in a way that it can be prepared immediately before use.

According to the invention, through the use of the compositions it is possible to avoid the abovementioned risks and side effects of surgical treatments and those arising from injectable lipodissolve agents at the currently used doses. In addition, this is a minimally invasive, outpatient treatment, showing great cost-effectiveness.

Contraindications for the use of systemic corticosteroids include diabetes, infectious illness, HIV, psychiatric disorders, SAH and other specific conditions.

Studies show that small doses of systemic corticosteroids for short periods of time can be considered safe, in patients without the above contra-indications. The doses for local injections (e.g. intra-articular, intrabursal, intradermal, intralesional) are given as ranges only. A safe dose of Triamcinolone is less than 0.15 mg/kg. The actual dosage depends upon the size of the joint of lesion and the severity of the condition being treated.

The safer use of corticosteroids refers to less than 1 week on the recommended doses. Frequent applications and high doses of these compounds can cause systemic side-effects. Even small doses, if used for long periods of time can also cause systemic side-effects.

Although the benefits of glucocorticoid therapy are derived from short-term vascular changes and limited immunosuppression, prolonged or high-dose glucocorticoid therapy has multiple side effects (*Pharmacol Ther* 2002; 96: 23-46). Glucocorticoid treatment can cause hypertension by two distinct mechanisms: one involves renal sodium retention and the ensuing increase in blood volume; a second results from potentiation of vasopressor responses to angiotensin II and catecholamines (*Cardiovas Res* 1999; 41:55-64). Even inhaled glucocorticoids are absorbed by the circulatory system and still cause side effects such as a decreased growth rate in children (*J Allergy Clin Immunol* 2003; 112: Suppl 3:s1-s40; *Arch Inter Med* 1999; 159:941-55).

The most known side-effects of the oral and parenteral use of corticosteroids are gland adrenal atrophy, cushing's syndrome, dyslipidemia, hypertension, thrombosis, vasculitis, changes in behavior, cognition, memory, and mood (i.e., glucocorticoid-induced psychoses), cerebral atrophy, gastrointestinal bleeding, pancreatitis, peptic ulcer, activation of latent viruses, opportunist infections, delayed wound healing, erythema, hypertrichosis, perioral dermatitis, petechiae, glucocorticoid-induced acne, striae rubrae distensae, telangiectasia, skin atrophy (including single injections of trancinolone on dose of 10 mg or 25 mg hydrocortisone), bone necrosis, muscle atrophy, osteoporosis, retardation of longitudinal bone growth, cataracts, glaucoma delayed puberty, fetal growth retardation, hypogonadism (*New England J Med* 2005; 353:1711-23; *British Journal of Rheumatology* 1991; 30:39-44).

Recently, a review showed that the side effects of short-term oral corticosteroids such avascular necrosis and a few cases of fatal varicella-zoster can occur in immunocompetent patients. Severe mood changes and psychotic reactions rarely occur unpredictably with short-term corticosteroids. These events are rare, and most treatments with short-term corticosteroid therapies are problem free. The literature reviewed clearly indicates that a short course of corticosteroids of 1 week, in the absence of specific contraindications, is unlikely to be harmful (psychotic or prepsychotic episodes possibly excepted (*J Cutan Med Surg.* 2008; 12(2):77-81).

Triamcinolone acetonide has been used as intravitreal injection with some complications like infectious endophthalmitis, transient central retinal artery occlusion, conjunctival ulcerations, retinal detachment and potential reactivation of a cytomegalovirus retinitis and posterior subcapsular cataract (*Ophthalmologe.* 2004 February; 101(2):121-8, *Ophtalmol.* 2008 September; 31(7):693-8; *J Drugs Dermatol.* 2008; 7(8):757-61). Intralesional triamcinolone acetonide has been used extensively for the treatment of hypertrophic and keloid scars. Complications are few, usually being local skin color changes, prominent vascular markings, or subcutaneous atrophy. Although, cushing's syndrome following intralesional administration of triamcinolone acetate has already been described (*Ann Plast Surg* 1996 May; 36(5): 508-11).

The term "intralesional injections" means injections applied into a specific area, condition or lesion. However, the administration of corticosteroids in the context of the invention is preferably carried out subcutaneously where fat deposits are located in the human faces and bodies.

Not only acetonide but also other forms of Triamcinolone, such as hexacetonide, can be used for parenteral and/or intralesional and/or subcutaneous injections. Short-acting injectable corticosteroids are preferable to be use in this medical indication.

Side-effects of intralesional injections of Triancinolone and other injectable corticosteroids in dermatology include skin discoloration, skin atrophy and risk of systemic side-effects, when high doses and frequent injections of this compound are used.

Pariser and Murray described a greater risk of cutaneous atrophy with concentrations above 5 mg/cm$^3$ of triamcinolone acetonide (Pariser H, Murray P F. *Intralesional Injections of Triamcinolone. Effects of different concentrations on psoriatic lesions. Arch Dermatol.* 1963 February; 87:183-7).

Injections into the superficial dermis can result in initial epidermal sloughing and persistent epidermal atrophy, whereas those in the deep dermis and subcutis may result in variable loss of fat with minimal epidermal change (Donofrio L M. *Panfacil volume restoration with fat. Dermatol Surg* 2005; 31: 1496-1505).

Besides skin atrophy, skin side effects arising from intralesional injections on the skin and/or subcutis include skin discoloration, asymmetries and volume reductions with consequent sagging of the superjacent skin. When the applications are done to the subcutaneous fat, these local side effects are mainly related to superficial injections. The risks of local side effects, such as skin necrosis and atrophies are rare; local atrophy may be wanted only for the fat tissue but not to the skin (epidermis and dermis).

The term "local anesthetic" means injectable and/or topical compounds. The Injectable anesthetic compounds are selected from mepivacaine, bupivacaine, ropivacaine; chloroprocaine, procaine, articaine/epinephrine and lidocaine and can be used as a diluent. Topical anesthetic creams or a cooler can be used to reduce the pain of the injections.

Local anesthetic solutions can or cannot contain a substance that causes vasoconstriction, such as adrenaline, phenylephrine and others. Vasoconstriction agents added to the anesthetic solution can limit and increase the local effects and also increase the safe dose of local anesthetics, from 4 to 7 mg/kg of lidocaine.

For the treatment of localized fat, the reasonable average recommended dose of Triamcinolone diluted in local anesthetic solution is 4 mg per month for 3 or 4 months.

The compositions of the invention are produced, for example, by dissolving 0.1 mL of Triamcinolone acetonide (40 mg/mL) and 0.2 mL of lidocaine with phenylephrine. It could be possible to add an anti-atrophy or lipodissolve agent.

The solution or dispersion containing the active drug (corticosteroids) is usually concentrated, and then a diluent is added to increase the dilution. In an alternative embodiment, the anesthetic solution is added as a diluent or in replacement of the diluent to increase the dilution and make the treatment more conformable for the patients. Production of the compositions of the invention are usually done at the moment of application.

Alternatively, the solution or dispersion containing the active drug (corticosteroids) is in a proper safe dose and appropriately diluted and it is at the physician's discretion to add or not to add the anesthetic solution.

Simultaneous introduction of the compositions and pharmaceutical forms employed according to the invention can also take place in particular applications via tumescence method which makes use of the hydrostatic pressure in order to ensure uniform distribution and to increase the safety and efficacy of the procedure. These can be achieved by dissolving the preparations of the invention in higher volumes of saline and/or other necessary pharmacological agents. Variations on the technique can also be done, by preceding the injection of the active drug (triamcinolone or similar) by local tumescent anesthesia.

In the context of the present invention, additional ingredients can be added to the formulation.

The composition(s) employed according to the invention, and comparable pharmaceutical forms, are administered by subcutaneous injections on the fat, also called "local" or "intralesional" injections. Subcutaneous injections at deep level is preferred for cosmetic lipoatrophy.

Suitable preparations and pharmaceutical forms can be suspensions, emulsions or injectable solutions, and products with protracted release of active ingredients. In order to increase the stability of the compositions and pharmaceutical forms of the invention, the preparations can also be in the form of a concentrate, dry substance or lyophilizates.

These pharmaceutical products are preferably produced and administered in dosage units, each unit comprising a particular dose of the composition(s) as active ingredient. In the case of solutions for injection in ampoule form, this dose can be adjusted, preferably from about 3 mg to 10 mg of Triancinolone acetonide, or equivalent doses of other injectable corticosteroids.

Monthly doses of solutions for injection required for the treatment of an adult patient are, depending on the size of the treated adipose tissue, from 3 mg to 10 mg, preferably 3 mg to 5 mg of Triancinolone acetonide, or equivalent doses of other injectable corticosteroids.

Suitable preparations and pharmaceutical forms to be injected can also be diluted before administration, preferably with saline solution. However, in some circumstances, higher or lower monthly doses may also be appropriate. The dose also depends on the area to be treated, the disease, condition or amount and/or thickness of the fat tissue to be treated Administration of the monthly dose can take place both through a single dose in the form of a single dosage unit or else a plurality of small dosages units and by multiple dosages of divided doses at defined intervals.

The term "subcutaneous derangements of fat distribution" means adipose tissues in the body of humans and animals which occur as genetically related or food-related depot of fat in the form of localized fat pads and can be regarded as esthetically disturbing critical zones such as abdomen, buttocks, hips, knee, calves, thighs, upper arm, chin, cheeks. They may also involve dystrophic proliferations of adipocytes such as benign proliferations of the fat cells like that occurring in lipomas.

The term "small localized area of fat accumulation" means all areas from 10 cm3 to 30 $cm^3$ of fat localized on the face or body that occurred due to an increase in the number or size of the fat cells. These include peribucal, eyebulging, submandibular, preaxillary fat, small raised areas in the abdomen and/or dorsum, love handles, raised areas on the buttocks, as well as excess response from surgical procedures such as liposuction and Subcision. These are usually considered cosmetic defects.

The term "adipocyte's atrophy" means decrease in the size and/or number of adipocytes as shown by skin biopsies. This adipocytes' atrophy leads to reduction of the treated small localized fat deposits.

Due to the extensive knowledge and published data, Triamcinolone and its derivatives, as well as other parenteral corticosteroids, are considered very safe. This patent reported a new potential use of local injections of triamcinolone, also called "local" or "intralesional injections", to induce cosmetic lipoatrophy of small localized fat deposits by reducing the size of the adipocites and fat thickness. This is a fast, efficient, cost-effective and low risk procedure, useful for cosmetic proposes.

Turning now to FIG. 1, a histologic picture is provided which shows fat tissue with hematoxilyn-eosin stain before treatment and the measurements of some adipocyes in pixels using same magnification.

Figure 2:
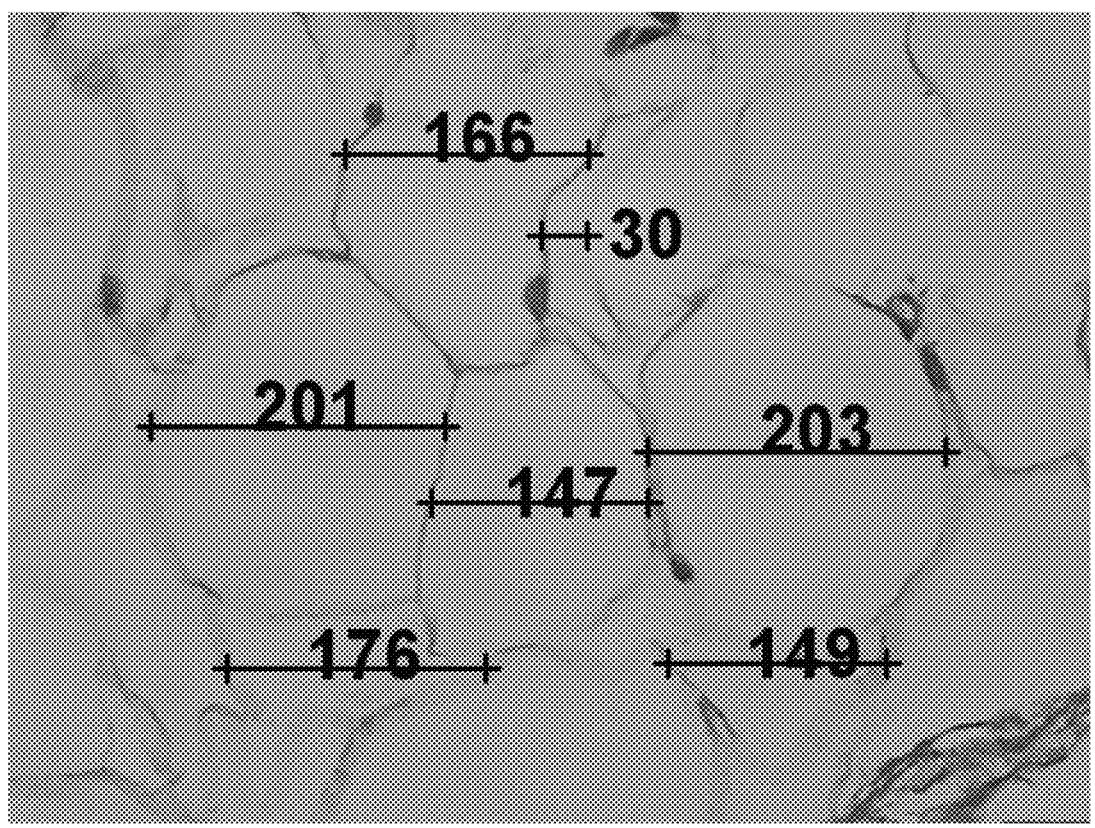
FIG. 2 provides a histologic picture which shows fat tissue with hematoxilyn-eosin stain after treatment and the measurements of some adipocyes in pixels using same magnification.

FIG. 2 is an histologic picture which shows a sample of fat tissue of the same area as FIG. 1, resulting from skin biopsy one month after single treatment with Triamcinolone local injections. There is a reduction on the average of the diameter of the adipocytes in the treated area.

FIGS. 1 and 2 show morphometry performed at the biopsies of the suprapubical area treated with a single injection of triamcinolone, before (FIG. 1) and one month after (FIG. 2). The average number of adipocytes observed in the optical field at the same magnification increased from 4 to 7 adipocytes per field. The average area of the adipocytes reduced from 31661 to 21705 pixels and their average diameters reduced from 190 to 153 pixels.

FIGS. 3 and 4 refer to MRI exams performed before (FIG. 3) and after (FIG. 4) single session of treatment with triamcinolone injections. There was a reduction of 27.3% of the thickness of the study area of facial fat before (1.1 cm) and after (0.8 cm) treatment.

Figures 5, 6:
FIG. 5 provides a view of a patient with marked areas for injection treatment, before treatment.
FIG. 6 provides a view of the same patient with marked areas for injection treatment one month after a single session.

FIGS. 5 and 6 show the same patient with marked areas for TA injections, before (FIG. 5) and one month after (FIG. 6) single session of TA injections.

FIG. 7 provides a flow chart of steps involved in an embodiment of treatment. The treatment begins by identifying a small fat deposit or a number of fat deposits to be reduced by treatment. The size of these deposits may be then determined. Next, an amount of corticosteroid is determined to reduce the size of the identified fat deposits. Once determined, a composition is injected into the fat deposit, the composition comprising the determined amount of corticosteroid, and optionally other components as described herein. This process may be repeated, for example, monthly, to maintain reduction of the fat deposits.

The present invention is described by the following example which is one of several embodiments.

EXAMPLE

A retrospective sample of treated patients is presented with the objective to describe a new therapeutic modality to treat small localized fat areas of the face, which interfere with youth and beauty of the face. Moreover, there is the need for minimally invasive treatment to safely treat small areas of localized fat on the face.

Research Design and Methods

A series of cases of small localized fat deposits on the face were treated with local triancinolone from March 2005 to October 2008 at a private clinic in Porto Alegre, southern of Brazil. Fifty six female patients with localized fat areas of the face were included in this sample. They received injections of triamcinolone (Kenalog®-40 Injection) diluted in anesthetic solution (0.02 g/mL Lidocaine plus 0.0004 g/mL Phenylephrine—Novocol®), in different concentrations and number of applications (up to 3 injections, once a month), according to patient's needs. The areas treated were mandibular and submental area, and, the inferior eyelids. Patients received injections in these fatty areas of the face, through a 0.3 cc BD Ultra Fine II syringe with short needle. All the injections were performed at the subcutaneous, 4 to 7 mm below the cutaneous surface. Small volumes (0.01 to 0.02) of the diluted triamcinolone were injected at 1 cm apart at the treated areas.

One patient was submitted to a facial Magnetic Resonance Imaging (MRI) exam before and after the triamcinolone injections, in order to show the results in terms of the changes in the thickness of subcutaneous tissue. Magnetic resonance imaging examination was performed with 1.5 Tesla Closed Bore Scanner (Magnetom Symphony Maestro Class, Siemens, Erlangen, Germany) with dedicated flexible coils. T1-weighted (600 ms/14 ms, Time Repetition/Time Echo) and T2-weighted (2500 ms/45 ms, TR/TE) turbo spin echo sequences were performed in coronal, axial and sagittal planes, with emphasis on the sagittal plane. An experienced radiologist evaluated the MRI images. The thickness of SQ adipose tissue was measured with Syngo software (Siemens, Erlangen, Germany) in millimeters (mm).

Another patient was submitted to 3 mm punch biopsies (one on the submental area and another on suprapubical area) before and after single treatment. Histological specimens of SQ tissue was stained with hematoxylin and eosin (HE stain) and also flow citometry was also performed in the histological images of before and after treatment samples.

Medical records included the main surgical cosmetic procedures carried out in association with triamcinolone injections, at the private dermatological clinic where the study took place.

The records of 56 patients with localized fat areas on the face that were treated with triamcinolone injections diluted in an anesthetic commercial composition were reviewed retrospectively. All patients were Caucasians women and the average of age was 57, 2±12, 2 years. Demographic data and characteristics of the triamcinolone applications were obtained from the clinical files, highlighting the main application areas, the dilution of the drug and the number of sessions. These data is presented in Table 1.

The physician who evaluated these subjects considered that they had good clinical and cosmetic improvement of facial contour due to reduction of the fatty areas, as shown in the before and after figures (FIGS. 4 and 5). Twenty seven patients have not returned for evaluation yet, so subject satisfaction and clinical improvement are missing.

High resolution MRI images performed in the axial plane demonstrated that there was significant reduction of the SQ adipose tissue at the treated area (mandibular). The reduction of the fat thickness showed by MRI was 37.5% at the mandibular area (from 0.8 to 0.5 cm) and 33.3% at the submental area (from 0.6 to 0.4 cm) (FIGS. 3 and 4)

Histological analysis demonstrated about 30% reduction in the volume of adipocytes in the sites of the injections, as shown in the before and after single treatment biopsies. Flow citometry results showed reduction in the average of the diameters of the adipocytes increase of the number of the adipocytes that were visualized per field at the same magnification field (from 4 to 7). (FIGS. 1 and 2)

A few local side-effects were observed in this group of the patients. The majority of the patients had pain and slight erythema during and immediately after the injections. Many patients presented hematomas in variable number and size, which disappeared spontaneously in a few days. No severe local or systemic side effects were observed in the patients treated with this new technique. No lab exams were done to evaluate potential systemic absorption of the drugs.

Cosmetic local side effects were presented by three patients, as described below:
one case of skin relief depression in the lower eyelid that appeared 2 months after the injection. No treatment was given and it disappeared after 1 months;
one case of skin and subcutaneous atrophies, caused by accidental superficial injections. This happened due to continuous talking by the patient during injections at the

TABLE 1

| Groups | Number of subjects | Age (years) | Average dose (mg) of triamcinolone (per session) | Average of volume (mL) administered of diluted triamcinolone | Average of volume of Anesthetic solution in the composition | Proportion of triamcinolone: and Anesthetic solution |
|---|---|---|---|---|---|---|
| Mandibular Area | 37 | 59 ± 12 | 5.2 | 0.13 | 0.27 | 1:2.1 |
| Submental Area | 11 | 52 ± 08 | 4.8 | 0.12 | 0.2 | 1:1.7 |
| Inferior Eyelids | 8 | 55 ± 16 | 3.2 | 0.08 | 0.16 | 1:2 |

Age was described in average ± Standard deviation.

Regarding the frequency of injections, they were performed as follow: one session for submental area; one or two sessions for infraorbital area (62.5% of this group of patients were submitted to one session, whereas 37.5% were submitted to two sessions); one to three sessions for the mandibular area (70.3% of this group of patients were submitted to one session, 27% were submitted to two sessions, and only 2.7% were submitted to three sessions).

Fifty seven percent of the patients underwent to another cosmetic procedure performed in the same day and surgical session. These patients received the triamcinolone injections and 30.3% received also fillers; 16% received also Botulinum Toxin (BT) and 10.71% received both (fillers and BT) combined with the Triamcinolone injections.

Twenty nine subjects (51.78%) returned to the clinic for evaluation. All of them were very satisfied with the results of the procedure and did not presented serious adverse events.

mandibular area. This was corrected with small volumes of an hyaluronic acid filler injections (Restylane—Q-Med);
one case of increased laxity of the mandibular skin was noted, although this patient never complained about this. This can be treated by radiofrequency of Infra-red light;
one case of asymmetry of the anterior fatty areas of neck. This was corrected with a second session of triancinolone injections. Sub-optimal response may also occur.

There is indication for a few monthly injections of the composition, due to the risk of systemic effects of corticosteroids.

CONCLUSION

The subcutaneous fat face is partitioned into discrete anatomic compartments: nasolabial fat, cheek fat, forehead and temporal fat, orbital fat and jowl fat.

A youthful face is characterized by the fullness and by a smooth transition between subcutaneous compartments. Facial aging is, in part, characterized by how these compartments change with age. Aging leads to abrupt contour changes between these regions, by volume loss and malposition of these compartments, in a number of causes[11]. A youth face looks like a triangle with its base up. In aged face, fat accumulation around the mandibular bone looks like a triangle with the base down.

Rare studies address solutions for the aged related facial fat deposits, which are a frequent complaint, and increase skin sagging. They usually are seeking for surgical procedures to correct these problems. (Hexsel D, Serra M, Mazzuco R, Dal'Forno T, Zechmeister D. *J Drugs Dermatol.* 2003 October, 2(5):511-8; Rotunda A M, Kolodney M S. *Dermatol Surg.* 2006; 32(4):465-80)

Small doses of triamcinolone in intralesional and local injections are largely used in dermatology for the treatment of many skin conditions, such as keloids and others. Due to the extensive knowledge and published data, intralesional injections of triamcinolone are considered very safe.

Intralesional corticosteroids injections release a high concentration of the drug directly on the action site, with minimal systemic absorption (Firozz, 1995) Among the many corticosteroids used for injections, triamcinolone and derivatives are more commonly used in dermatology (Firozz, 1995) and triamcinolone is the more acceptable due to its physical characteristics (Callen, 1981).

This patent application reports a new potential use of this drug in intralesional and local injections, to induce cosmetic lipoatrophy of the face by reducing the size of the adipocytes as well as in the fat thickness.

This is a fast, efficient, cost-effective and low risk minimally invasive procedure, useful for cosmetic proposes.

The invention claimed is:

1. An injectable composition selected and configured to reduce small areas of subcutaneous accumulation of fat comprising:
   0.1 mL of triamcinolone acetonide at a concentration of 40 mg/mL;
   0.2 mL of a solution of 0.02 g/mL of lidocaine and a vasoconstriction agent selected from the group consisting of phenylephrine or epinephrine;
   in a saline or physiological pH solution.

2. An injectable composition selected and configured to reduce small areas of subcutaneous accumulation of fat consisting of:
   0.1 mL of triamcinolone acetonide at a concentration of 40 mg/mL;
   0.2 mL of a solution of 0.02 g/mL of lidocaine and a vasoconstriction agent selected from the group consisting of phenylephrine or epinephrine;
   in a saline or physiological pH solution.

3. The injectable composition of claim 1 wherein the vasoconstriction agent is a solution of 0.0004 g/mL of phenylephrine.

4. The injectable composition of claim 2 wherein the vasoconstriction agent is a solution of 0.0004 g/mL of phenylephrine.

* * * * *